US012675753B2

(12) United States Patent
Eggenberger et al.

(10) Patent No.: US 12,675,753 B2
(45) Date of Patent: *Jul. 7, 2026

(54) ORCHESTRATING VEHICLES AND REMOTE OPERATING CLIENTS

(71) Applicant: International Business Machines Corporation, Armonk, NY (US)

(72) Inventors: Christian Eggenberger, Wil (CH); Kavitha Hassan Yogaraj, Bangalore (IN); Aaron K. Baughman, Cary, NC (US); Markus Van Kempen, Toronto (CA)

(73) Assignee: International Business Machines Corporation, Armonk, NY (US)

( * ) Notice: Subject to any disclaimer, the term of this patent is extended or adjusted under 35 U.S.C. 154(b) by 227 days.

This patent is subject to a terminal disclaimer.

(21) Appl. No.: 18/053,433

(22) Filed: Nov. 8, 2022

(65) Prior Publication Data

US 2024/0161028 A1    May 16, 2024

(51) Int. Cl.
G06Q 10/0631 (2023.01)
A61B 5/00 (2006.01)
G05D 1/00 (2024.01)

(52) U.S. Cl.
CPC ... G06Q 10/063114 (2013.01); G05D 1/0011 (2013.01); A61B 5/00 (2013.01)

(58) Field of Classification Search
CPC ......... G06Q 10/063114; G05D 1/0011; G05D 1/2247; G05D 1/227; G05D 1/6987;
(Continued)

(56) References Cited

U.S. PATENT DOCUMENTS 4,855,822 A      8/1989  Narendra et al.
5,448,479 A *    9/1995  Kemner .............. G05D 1/0061
                                                         701/2
(Continued)

FOREIGN PATENT DOCUMENTS

CN      114483947 A    5/2022
EP        3499405 A1    6/2019
(Continued)

OTHER PUBLICATIONS

"5G Remote Driving Test Connecting Tokyo and Germany", https://www.sony.com/en/SonyInfo/vision-s/news.html#entry15, (Retrieved Oct. 19, 2022), 9 pages.
(Continued)

*Primary Examiner* — Donald J Wallace
*Assistant Examiner* — Jalal C Coduroglu
(74) *Attorney, Agent, or Firm* — CANTOR COLBURN LLP; Kelsey M. Skodje

(57)    ABSTRACT

A computer-implemented method for orchestrating operation of multiple vehicles includes detecting, based on a monitoring of a first remote operating client assigned to control the multiple vehicles, that the first remote operating client is to be replaced. Further, the method includes identifying, from multiple remote operating clients, a second remote operating client as a replacement of the first operating client, the identifying includes determining compatibility of the second remote operating client with the multiple vehicles. Further, the method includes reassigning control of the multiple the vehicles to the second remote operating client, which provides an operation instruction to manipulate operation of the multiple vehicles.

20 Claims, 8 Drawing Sheets

(58) Field of Classification Search

CPC .......... G05D 2101/15; G05D 2105/22; G05D 2107/13; G05D 2109/10; A61B 5/00; A61B 2503/22; A61B 5/18

See application file for complete search history.

(56) References Cited

U.S. PATENT DOCUMENTS

| | | | |
|---|---|---|---|
| 5,596,319 | A | 1/1997 | Spry |
| 8,750,645 | B2 | 6/2014 | Joshi et al. |
| 10,347,130 | B2 | 7/2019 | Cho et al. |
| 10,437,247 | B2 | 10/2019 | Patel et al. |
| 11,079,753 | B1 | 8/2021 | Roy |
| 11,656,096 | B1 | 5/2023 | Freydin et al. |
| 2008/0027591 | A1* | 1/2008 | Lenser ................. G05D 1/0038 |
| | | | 701/28 |
| 2011/0288714 | A1 | 11/2011 | Flohr et al. |
| 2015/0307024 | A1 | 10/2015 | Fukuda et al. |
| 2017/0015405 | A1 | 1/2017 | Chau et al. |
| 2017/0045885 | A1 | 2/2017 | Okumura et al. |
| 2017/0154052 | A1 | 6/2017 | Hassanzadeh et al. |
| 2017/0251195 | A1 | 8/2017 | Niehsen |
| 2018/0075575 | A1 | 3/2018 | Bostick et al. |
| 2019/0039613 | A1 | 2/2019 | Lee et al. |
| 2019/0150331 | A1 | 5/2019 | Watanabe |
| 2019/0193659 | A1 | 6/2019 | Miyazawa et al. |
| 2020/0062267 | A1* | 2/2020 | Magzimof .......... B60W 50/082 |
| 2020/0126179 | A1 | 4/2020 | Yan et al. |
| 2021/0064020 | A1 | 3/2021 | Cutu |
| 2021/0116907 | A1* | 4/2021 | Altman ................... G05D 1/223 |
| 2021/0349460 | A1 | 11/2021 | Huang et al. |
| 2022/0073083 | A1* | 3/2022 | Magzimof ............ B60W 40/09 |
| 2022/0137621 | A1* | 5/2022 | Buttolo ................... G01S 19/42 |
| | | | 701/2 |
| 2022/0156665 | A1* | 5/2022 | Beth .................... G05D 1/0276 |
| 2022/0282451 | A1 | 9/2022 | Ready-Campbell et al. |
| 2022/0398806 | A1 | 12/2022 | Arksey et al. |
| 2023/0192124 | A1 | 6/2023 | Winter et al. |
| 2024/0118693 | A1* | 4/2024 | Urano .................. G05D 1/0055 |
| 2024/0160203 | A1 | 5/2024 | Eggenberger et al. |
| 2024/0391112 | A1 | 11/2024 | Hirai et al. |

FOREIGN PATENT DOCUMENTS

| | | |
|---|---|---|
| WO | 2019150331 A1 | 8/2019 |
| WO | 2020/003392 A1 | 1/2020 |

OTHER PUBLICATIONS

"Drivers Can Work Remotely, Too", https://phantom.auto/, (Retrieved Oct. 19, 2022), 7 pages.

Remote Control: Companies Researching Teleoperation for Autonomous Vehicles, https://www.cbinsights.com/research/autonomous-vehicle-teleoperation-patents/, (Retrieved Oct. 19, 2022), 9 pages.

"Safe Teleoperation to Enable Autonomous Vehicles—Today!", https://iot-automotive.news/deutsche-telekom-the-new-long-distance-drivers-in-the-office-and-4000-kilometers-away/, (Retrieved Oct. 19, 2022), 5 pages.

Blanco, "Startup's Autonomy Workaround: 'Teledrivers' to Operate Cars from Remote Location", Car and Driver; https://www.caranddriver.com/news/a37648114/vay-autonomous-teledriver-startup/, (Retrieved Oct. 19, 2022), 6 bages.

Daskalakis, et al. "Mechanism design via optimal transport", EC '13: ACM Conference on Electronic Commerce, 2013, 28 pages.

Demir, "What is Volumetric Video? The Future of Video Technologies", https://antmedia.io/what-is-volumetric-video/, (Retrieved Dec. 18, 2022), 12 pages.

Eggenberger et al., "Orchestrating Vehicles and Remote Operating Clients," U.S. Appl. No. 18/053,436, filed Nov. 8, 2022.

Halpern, "The Rise of A.I. Fighter Pilots", https://www.newyorker.com/magazine/2022/01/24/the-rise-of-ai-fighter-pilots, (Retrieved Oct. 19, 2022), 22 pages.

Ison, et al, "Learning efficient control of robots using myoelectric interfaces," 2014 IEEE International Conference on Robotics and Automation (ICRA), 2014, 6 pages.

Juliussen, "Why Autonomous Vehicles Will Need Teleoperation", https://www.eetasia.com/why-autonomous-vehicles-will-need-teleoperation/, (Retrieved Oct. 19, 2022), 8 pages.

Li, et al, "Learning to Match Via Inverse Optimal Transport", The Journal of Machine Learning Research, vol. 20, Issue 1; 2021, pp. 1-37.

List of IBM Patents or Patent Applications Treated as Related; Date Filed: Nov. 8, 2022; 2 pages.

Paulin, et al, "Sliced Optimal Transport Sampling", ACM Transactions on Graphics, vol. 39, Issue 4, 2020, 17 pages.

Podhurst, "Autonomous Vehicle Teleoperation: Is one Network Enough for Remote Driving?", https://driveu.auto/blog/autonomous-vehicle-teleoperation-is-one-network-enough-for-remote-driving/, (Retrieved Oct. 19, 2022), 10 pages.

Rosenzweig, "Teleoperation: Indirect Control Methods for Autonomous Vehicles", https://www.therobotreport.com/teleoperation-indirect-control-methods-for-autonomous-vehicles/, (Retrieved Oct. 19, 2022), 12 pages.

Saha, et al, "Exploring Multiobjective Optimization for Multiview Clustering" ACM Transactions on Knowledge Discovery from Data; vol. 12, 2018; pp. 1-30.

Thakallapelli, et al., "Real-time Frequency Based Reduced Order Modeling of Large Power Grid", 5 pages.

Venugopalan, et al., "Translating Videos to Natural Language Using Deep Recurrent Neural Networks", arXiv, 2014, 11 pages.

Yurochkin, et al, "Hierarchical Optimal Transport for Document Representation", 33rd Conference on Neural Information Processing Systems, 2019, pp. 1-17.

* cited by examiner

502A

408

405

| Objective Criteria | Minimizing overall Operating Cost | Smooth Journey (e.g., avoidance of potholes) | Shortest Travel Time | Response Time of Remote Driver | No. of Vehicles assigned to one Remote Driver | Views |
|---|---|---|---|---|---|---|
| Objective | min. | max. | min. | min. | max. | |
| Driving Permits for Vehicle Types | | | | | | Rating of Remote Driver g (1) |
| Certification Level for Remote Controlled, Simultaneous Driving of Vehicles | | | | | | |
| Driven Miles without Accident | | | | | | |
| Driven Miles in Urban or Rural Areas | | | | | | |
| No. of Traffic Tickets in the Last n Months | | | | | | |
| Driving Experience on the Current Route (Frequency) | | | | | | |
| Number of Driven Hours without Break | | | | | | (2) |
| Biometric Data (e.g., HRV, Brainwave, Eyelid Movement, Blood Sugar) | | | | | | |
| Network Service Quality (e.g., Throughput, Latency, Jitter, Error Rate) | | | | | | State of IT-Infrastructure for Remote Driver g for Vehicle i (3) |
| Edge Computing Performance (e.g., Satellite Cloud, Cloud) | | | | | | |
| Computer Capacity / Performance at the Remote Driver site | | | | | | |
| Monitor Equipment (e.g., Number of Monitors and their Specifications) | | | | | | |
| Control Devices to drive one or several Vehicles in parallel (e.g., Joystick, Pedals) | | | | | | |

FIG. 5A

| | | | | | Objective Criteria | | |
|---|---|---|---|---|---|---|---|
| Minimizing overall Operating Cost | Smooth Journey (e.g., avoidance of potholes) | Shortest Travel Time | Response Time of Remote Driver | No. of Vehicles assigned to one Remote Driver | | | |
| min. | max. | min. | min. | max. | Objective | Views | |
| | | | | | Street Condition (e.g., Dry, Icy, Risk of Aquaplaning, Tarred, Gravel) | 4 | Classification of Current Street Situation for Vehicle i |
| | | | | | Weather Condition (e.g., Wind, Visability) | | |
| | | | | | Seasonal Conditions (e.g., Animal Crossings such as Moose, Wild Boar, etc.) | | |
| | | | | | Time of Day (e.g. Sunrise, Sunset, Night) | | |
| | | | | | Traffic News (e.g., Traffic Congestion, Ghost Driver) | 5 | |
| | | | | | Police Accident Protocols | | |
| | | | | | Clarity (e.g., Flat Terrain, Urban Canyons) | | |
| | | | | | Slope | | |
| | | | | | Number of Lanes | | |
| | | | | | Road Width | | |
| | | | | | Curve Radius | | |
| | | | | | Speed Limit | | |
| | | | | | Level of Autonomous Driving (e.g., SAE Level 0-5) | 6 | Technology State of Vehicle i |
| | | | | | Stopping Distance (e.g. based on tire type (seasonal tires), tire condition, payload) | | |
| | | | | | Driving physics mainly defined by the Design & the Effect of External Forces | | |

ORCHESTRATING VEHICLES AND REMOTE OPERATING CLIENTS

BACKGROUND

The present invention relates to computing technology, network technology, sensor technology, and automotive technology, and particularly orchestrating remote operation of vehicles using remote clients.

Here, "automotive" can include ground vehicles, aquatic vehicles, aviation vehicles, space travel vehicles, etc., which may be used for private and/or public transportation, goods transportation, surveillance, or any other purpose. Such automotives can include cars, trucks, airplanes, ships, submarines, rockets, satellites, drones, etc. Unmanned Vehicles (UVs) include Unmanned Underwater Vehicles (UUVs), Unmanned Surface Vehicles (USuVs), Unmanned Ground Vehicles (UGVs), Unmanned Aerial Vehicles (UAVs), and Unmanned Space Vehicles (USpVs). UVs can be used for applications where it may be inconvenient, dangerous, or impossible to have a human operator present. UVs may be expendable or recoverable and can be operated autonomously or remotely. Accordingly, a typical UV includes cameras and other surveillance equipment (e.g., sensors) that capture surrounding information. The UV will typically either autonomously make decisions about the information or pass the information to a human operator at a different location who will control the vehicle remotely.

SUMMARY

According to one or more embodiments of the present invention, a computer-implemented method for orchestrating operation of a plurality of vehicles includes generating a single display image stream based on a plurality of image streams, each image stream corresponding to a respective vehicle from the plurality of vehicles, the plurality of vehicles being assigned to be controlled by a remote operating client. The method further includes receiving, from the remote operating client, a vehicle operation instruction in response to the single display image stream being displayed by the remote operating client. The method further includes transmitting, to at least one vehicle from the plurality of vehicles, the operation instruction to manipulate operation of the at least one vehicle.

According to one or more embodiments of the present invention, a system includes a computer server configured to orchestrate operation of multiple vehicles based on instructions from a remote operating client by performing a computer-implemented method. The method includes generating a single display image stream based on a plurality of image streams, each image stream corresponding to a respective vehicle from the plurality of vehicles, the plurality of vehicles is assigned to be controlled by the remote operating client. The method further includes receiving, from the remote operating client, a vehicle operation instruction in response to the single display image stream being displayed by the remote operating client. The method further includes transmitting, to at least one vehicle from the plurality of vehicles, the operation instruction to manipulate operation of the at least one vehicle.

According to one or more embodiments of the present invention, a computer program product includes a memory device with computer-executable instructions therein, the computer-executable instructions when executed by a processing unit perform a method to orchestrate operation of multiple vehicles. The method includes generating a single display image stream based on a plurality of image streams, each image stream corresponding to a respective vehicle from the plurality of vehicles, the plurality of vehicles being assigned to be controlled by a remote operating client. The method further includes receiving, from the remote operating client, a vehicle operation instruction in response to the single display image stream being displayed by the remote operating client. The method further includes transmitting, to at least one vehicle from the plurality of vehicles, the operation instruction to manipulate operation of the at least one vehicle.

According to one or more embodiments of the present invention, a computer-implemented method for orchestrating operation of multiple vehicles includes detecting, based on a monitoring of a first remote operating client assigned to control the multiple vehicles, that the first remote operating client is to be replaced. Further, the method includes identifying, from multiple remote operating clients, a second remote operating client as a replacement of the first operating client, the identifying includes determining compatibility of the second remote operating client with the multiple vehicles. Further, the method includes reassigning control of the multiple vehicles to the second remote operating client, which provides an operation instruction to manipulate operation of the multiple vehicles.

According to one or more embodiments of the present invention, a system includes a computer server to orchestrate remote operation of vehicles by performing a computer-implemented method that includes detecting, based on a monitoring of a first remote operating client assigned to control the multiple vehicles, that the first remote operating client is to be replaced. Further, the method includes identifying, from multiple remote operating clients, a second remote operating client as a replacement of the first operating client, the identifying includes determining compatibility of the second remote operating client with the multiple vehicles. Further, the method includes reassigning control of the multiple vehicles to the second remote operating client, which provides an operation instruction to manipulate operation of the multiple vehicles.

According to one or more embodiments of the present invention, a computer program product includes a memory device with computer-executable instructions therein, the computer-executable instructions when executed by a processing unit perform a method to orchestrate remote operation of vehicles, the method includes detecting, based on a monitoring of a first remote operating client assigned to control the multiple vehicles, that the first remote operating client is to be replaced. Further, the method includes identifying, from multiple remote operating clients, a second remote operating client as a replacement of the first operating client, the identifying includes determining compatibility of the second remote operating client with the multiple vehicles. Further, the method includes reassigning control of the multiple vehicles to the second remote operating client, which provides an operation instruction to manipulate operation of the multiple vehicles.

Embodiments of the invention described herein address technical challenges in vehicle operation, particularly in fields of remote operation of vehicles.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings.

FIGS. 5A and 5B depict an example view of several objectives used in an example scenario according to one or more embodiments of the present invention;

Figure 1:
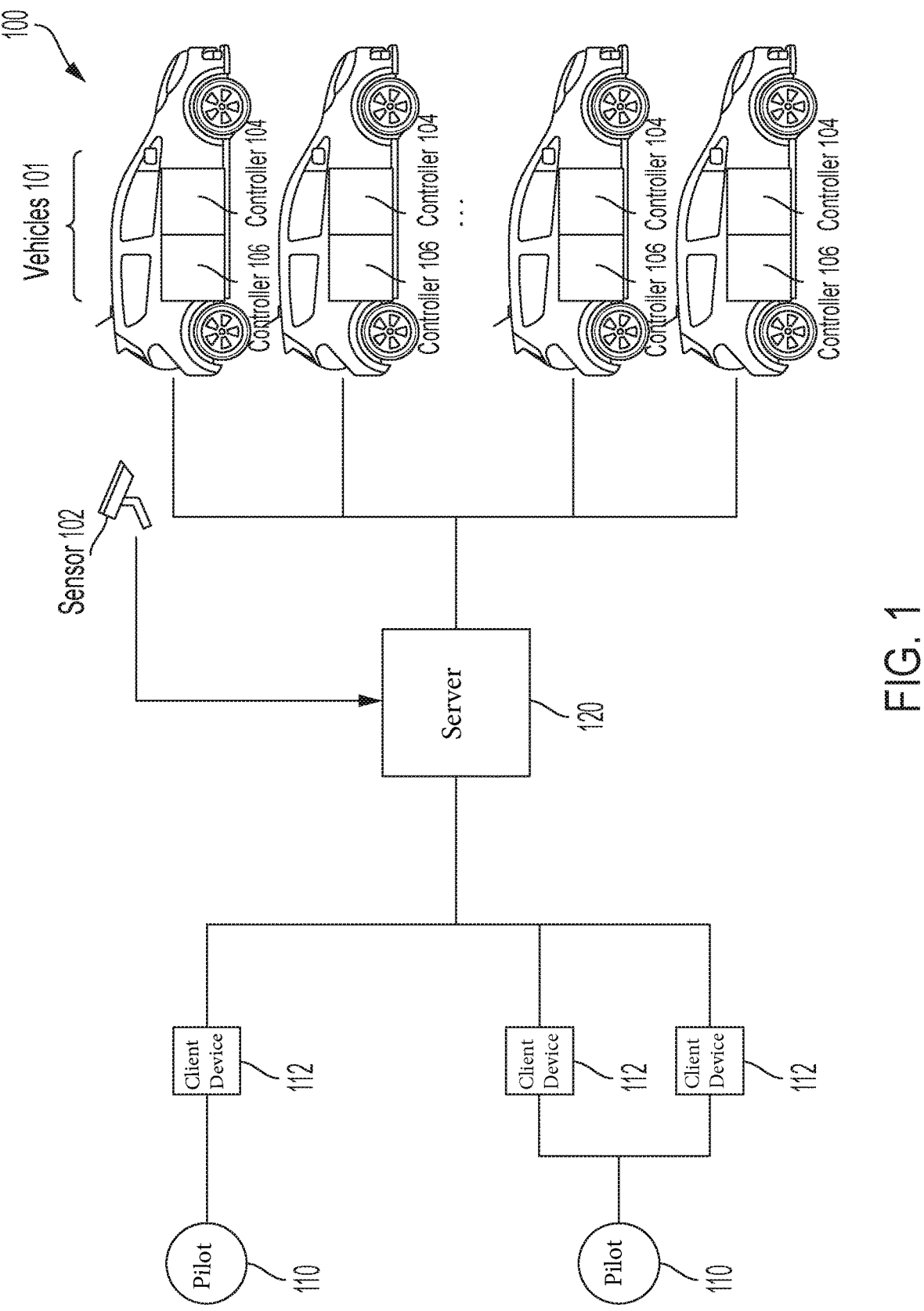
FIG. 1 depicts a remote vehicle control system according to one or more embodiments of the present invention.

The diagrams depicted herein are illustrative. There can be many variations to the diagrams, or the operations described therein without departing from the spirit of the invention. For instance, the actions can be performed in a differing order, or actions can be added, deleted, or modified. Also, the term "coupled," and variations thereof describe having a communications path between two elements and do not imply a direct connection between the elements with no intervening elements/connections between them. All of these variations are considered a part of the specification.

In the accompanying figures and following detailed description of the disclosed embodiments, the various elements illustrated in the figures are provided with two or three-digit reference numbers. With minor exceptions, the leftmost digit(s) of each reference number corresponds to the figure in which its element is first illustrated.

DETAILED DESCRIPTION

Embodiments of the invention described herein address technical challenges in automotive/vehicle technology, particularly used in the fields of remote controlled vehicles, which may be Unmanned Vehicles (UVs), autonomous vehicles, or a combination thereof. One or more embodiments of the present invention facilitate improvements to remotely controlled (or remotely operated) vehicles, and a system that facilitates remote controlling of vehicles. For example, embodiments of the present invention facilitate a pilot (or operator) to control one or more vehicles simultaneously (1:n). Alternatively, or in addition, several pilots can control one or more vehicles simultaneously (n:m). Further, one or more embodiments of the present invention facilitate generating display streams for the pilots, by determining how much each image (captured by sensors associated with the vehicles) is to be changed to be equivalent to another image that is being displayed to a pilot. For example, an image stream displayed to a pilot for teleoperating multiple vehicles is changed to generate a singular image stream based on which, a single pilot can control the multiple vehicles.

Embodiments of the present invention further facilitates mapping of controls between a transport scene (generated based on multiple image streams) to a raw scene using a machine learning (ML) system. The trained ML system, for example, shows areas on an augmented reality displays that can be identified or not. Composing the multiple image streams can include superimposing hazards or situations that are not present in reality, or which cannot be identified/classified by the ML system, but to which the pilots have to react in time and correctly.

Further, one or more embodiments of the present invention facilitate determining, based on biometric data (e.g., Heart Rate Variability (HRV), blood sugar level, eyelid movement, eye movement, beta waves), and the quality of the response (correctness and the reaction speed), a state of the pilot.

Further, one or more embodiments of the present invention facilitate continuously determining an optimal number of pilots per vehicle and/or, conversely, an optimal number of vehicles per pilot. In some embodiments of the present invention, the optimal numbers are determined using ML, such as a multi-view clustering multi-objective approach.

Further yet, in one or more embodiments of the present invention, an image stream (sometimes also referred to as computer vision stream, or video stream) of data is converted into actionable commands for vehicles by converting video streams to scene understanding (e.g., words), and subsequently, words from pilots to commands for vehicles to perform. The scene understanding can be used for composing the display stream presented to the pilots in one or more embodiments of the present invention. Alternatively, or in addition, the scene understanding is used to record one or more situations and the pilot's responses in such situations are also recorded.

Based on the scene understanding, as well as the one or more measurements of the pilots, embodiments of the present invention facilitate checking compatibility of different multi views of the pilots and multi objective optimization on capability of the pilots. For example, scene understanding by cameras in vehicles can be used as an objective function.

FIG. 1 depicts a remote vehicle control system according to one or more embodiments of the present invention. The system 100 comprises vehicles 101, a computer server 120, and remote pilots (operators) 110.

Although the vehicles 101 are depicted as "cars," it is understood that the vehicles 101 can be any type of vehicle, such as a truck, a van, a train, a boat, an aircraft, etc. Further, the N vehicles 101 do not have to be of the same type. The system 100 can have N vehicles 101, N≥1. Each vehicle 101 has one or several respective controllers (e.g., Electronic Control Unit (ECU)) 104. The controller 104 can facilitate performing one or more operations of the vehicle 101, for example, controlling heading (direction), velocity (or speed), acceleration, braking, etc. to navigate the vehicle 101. In some embodiments, the controller 104 facilitates autonomous driving, semi-autonomous driving, or any other level of autonomy of controlling the vehicle 101 as may be defined by one or more standardizations. Alternatively, or in addition, the controller 104 can facilitate operations, such as controlling windows, infotainment system, charging/fueling, controlling windshield wipers, controlling air conditioner/heater, etc., which may not be directly related to navigating the vehicle 101.

The controller 104 can include one or more processing units. Further, the controller 104 can perform one or more operations based on one or more measurements received from one or more sensors 106 of the vehicle 101. The sensors 106 can include tire pressure sensors, humidity sensor, light sensors, proximity sensors, motion sensors, global positioning system (GPS), radars, lidars, cameras, etc. The measurements from the sensors 106 can be used independently and/or in a fused manner (sensor fusion). In some cases, the controller 104 can determine and perform operations locally (i.e., by itself) by processing measurements from the one or more sensors 106. For example, starting/stopping windshield wipers may be performed based on processing of measurements from a humidity sensor. In other cases, the controller 104 transmits the information from the sensors 106 to the server 120, which is at a remote location, for processing. The controller 104 performs one or more operations based on instructions received from the server 120.

The vehicle 101 and the server 120 communicate with each other via one or more communication networks using known or later developed protocols. For example, the communication networks can include 4G, 5G, LTE, or any other type of network or a combination thereof. Each of the N vehicles 101 can communicate with the server 120.

The server 120 receives data from and transmits data to the vehicles 101. For example, the server 120 receives sensor information from the vehicles 101. The server 120 can also receive other types of data from the vehicles 101, for example, occupant data, occupant provided data, etc.

In some embodiments of the present invention, the server 120 also receives information about the vehicles 101 from one or more sensors 102 that are external to the vehicles 101. For example, the sensors 102 can be part of infrastructure, such as traffic control, highway management, department of transportation (DOT), etc. For example, the sensors 102 can include traffic cameras, speed sensors, radars, lidars, or any other type of sensors that are part of the infrastructure and are external to the vehicles 101. The sensors 102 can provide information, such as vehicle position, vehicle speed, heading, surroundings (pedestrians, buildings, objects, structures, intersections, traffic light/signal conditions, etc.) about one or more specific vehicle 101. In some embodiments of the present invention, the information provided by the sensors 102 includes identification(s) of the one or more vehicles 101 that are associated with the information transmitted. For example, the identification can include license plate number, color, make, model, or other electronic identifier (e.g., RFID, machine-readable code (quick response code, barcode, etc.)), or a combination thereof.

The server transmits one or more instructions to the vehicles 101. The instructions can include operation instructions that cause navigation of the vehicle 101. For example, the operation instructions change at least speed and heading of the vehicle 101. Alternatively, or in addition, the instructions can include operation instructions to change state of one or more components of the vehicle 101. The instructions can also include queries to one or more occupants of the vehicle 101.

In some embodiments, the server 120 determines and provides the instructions to the vehicle 101 based on processing of the information received from the vehicle 101. Alternatively, or in addition, the server 120 provides the instructions based on those received from the pilots 110.

The pilots 110 provide instructions for the vehicle 101 to the server 120 via one or more remote operating clients 112 (referred to as client devices). The pilots 110 determine the instructions based on the information received from the vehicles 101. A pilot 110 is a human operator. Each pilot 110 has at least one client device 112. Each pilot 110 operates at least one of the N vehicles 101 using the client device(s) 112. That is there can be a m: n relation between the pilots 110 and the vehicles 101. As will be described further the relationship can be dynamically updated based on one or more stated predetermined objectives.

The client devices 112 facilitate communication of the pilots 110 with the server 120. The client devices 112 and the server 120 communicate via the one or more communication networks. The communication facilitates the pilot 110 to receive information from the vehicle 101, and in response determine, and provide an appropriate operation instruction for the vehicle 101. The client devices 112 facilitate the pilots 110 to receive the information from the vehicles 101 assigned to the pilots 110, and the pilots 110 to provide instructions to the vehicles 101.

Figure 2:
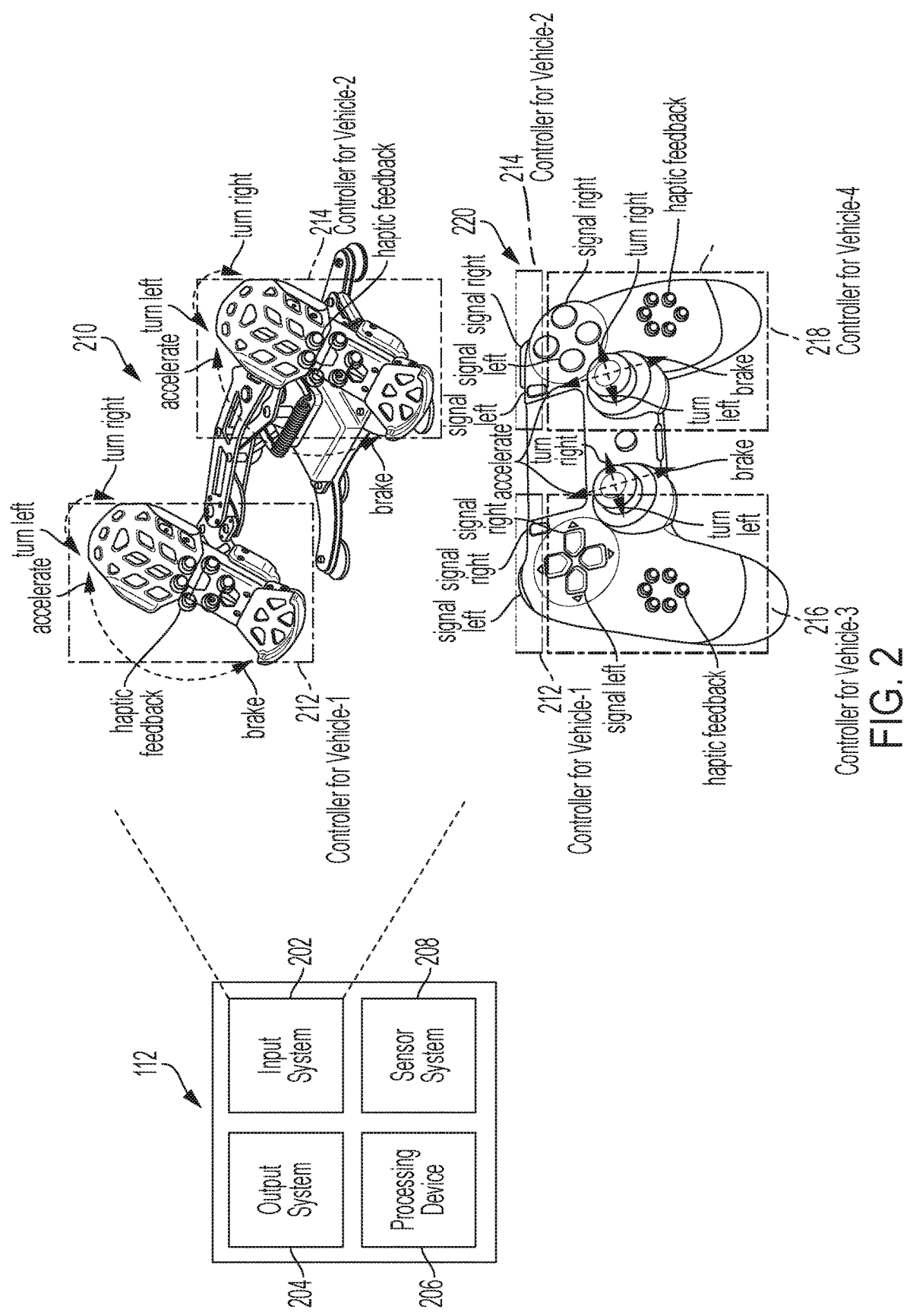
FIG. 2 depicts an example block diagram of a remote client device according to one or more embodiments of the present invention.

FIG. 2 depicts an example block diagram of a remote client device 112 according to one or more embodiments of the present invention. The client device 112 includes an input system 202, an output system 204, a processing system 206, and a sensor system 208, among other components.

The output system 204 of the client device 112 includes display devices, audio devices, haptic devices, etc. that facilitate providing information received from the server (e.g., vehicle information) to the pilots 110.

The processing system 206 can include one or more processors (e.g., microprocessors, graphic processors, arithmetic logic units, digital signal processors, etc.) along with other devices such as memory, cache, mother boards, power circuits, etc. that facilitate the operation of the client device 112.

The input system 202 of the client device 112 includes input devices that the pilots 110 can use to provide one or more operations which are translated into instructions that the vehicles 101 can execute upon receipt. The input system 202 can include several types of controllers, such as a steering controller (210), game controller (220), keyboard (not shown), mouse (not shown), joystick (not shown), or any other types of input controllers or a combination thereof. The input system 202 can include two or more input controllers that are used simultaneously in some embodiments of the present invention. In one or more embodiments of the present invention, each input controller (210, 220) can be used for multiple vehicles 101.

For example, the steering controller 210 and the game controller 220 that are depicted can include a first control-pad 212 that is assigned to generate operational instructions for a first vehicle 101, a second control-pad 214 that is assigned to generate operational instructions for a second vehicle 101, a third control-pad 216 that is assigned to generate operational instructions for a third vehicle 101, and a fourth control-pad 218 that is assigned to generate operational instructions for a fourth vehicle 101. By using the steering controller 210 and the game controller 220, a remote pilot 110 can operate at least four (4) remote vehicles 101 simultaneously. The operational instructions are generated by the pilot 110 interacting with one or more interactive elements (e.g., buttons, joysticks, pedals, steering wheel, etc.) of the input controllers (210, 220). For example, operational instructions can include changing heading (e.g., turn left, turn right), changing speed (e.g., accelerate, brake), changing signals (e.g., signal left, signal right), changing infotainment (e.g., change radio station, change media), etc.

In some embodiments of the present invention, the input system 202 can also provide feedback to the pilot (i.e., be part of the output system 204). For example, the input controllers (210, 220) can provide feedback, e.g., haptic feedback to the pilot 110.

The sensor system 208 includes one or more sensors that measure a state of the pilot 110 that is using the client device 112. For example, the sensor system 208 can include sensors that record the pilot's 110 biometric signals, such as heartbeat, temperature, blood pressure, oxygen level, etc. The sensor system 208 can further keep track of the pilot's eyes, posture, head position, etc. Alternatively, or in addition, the sensor system 208 can also measure and record the pilot's 110 blood alcohol level, or another chemical breakdown. Such measurements may be captured in a continuous or discrete manner. Based on the captured measurements, the control device 112 (or server 120) may determine a state of the pilot 110. For example, the state can include predetermined list, such as awake, tired, sleepy, needs-rest, etc. Based on the state, the system 100 can determine whether the pilot 110 be left in his/her current assignment with no changes, an additional vehicle be assigned to him/her to control (operate/supervise), another pilot/supervisor assist him/her, or he/she be relieved so that he/she can take a recovery break or leave work. In other examples, the number of states, or the states themselves can vary. Some other types of measurements captured can be listed elsewhere in the description herein. Other determinations may be made in other embodiments of the present invention.

Figure 3:
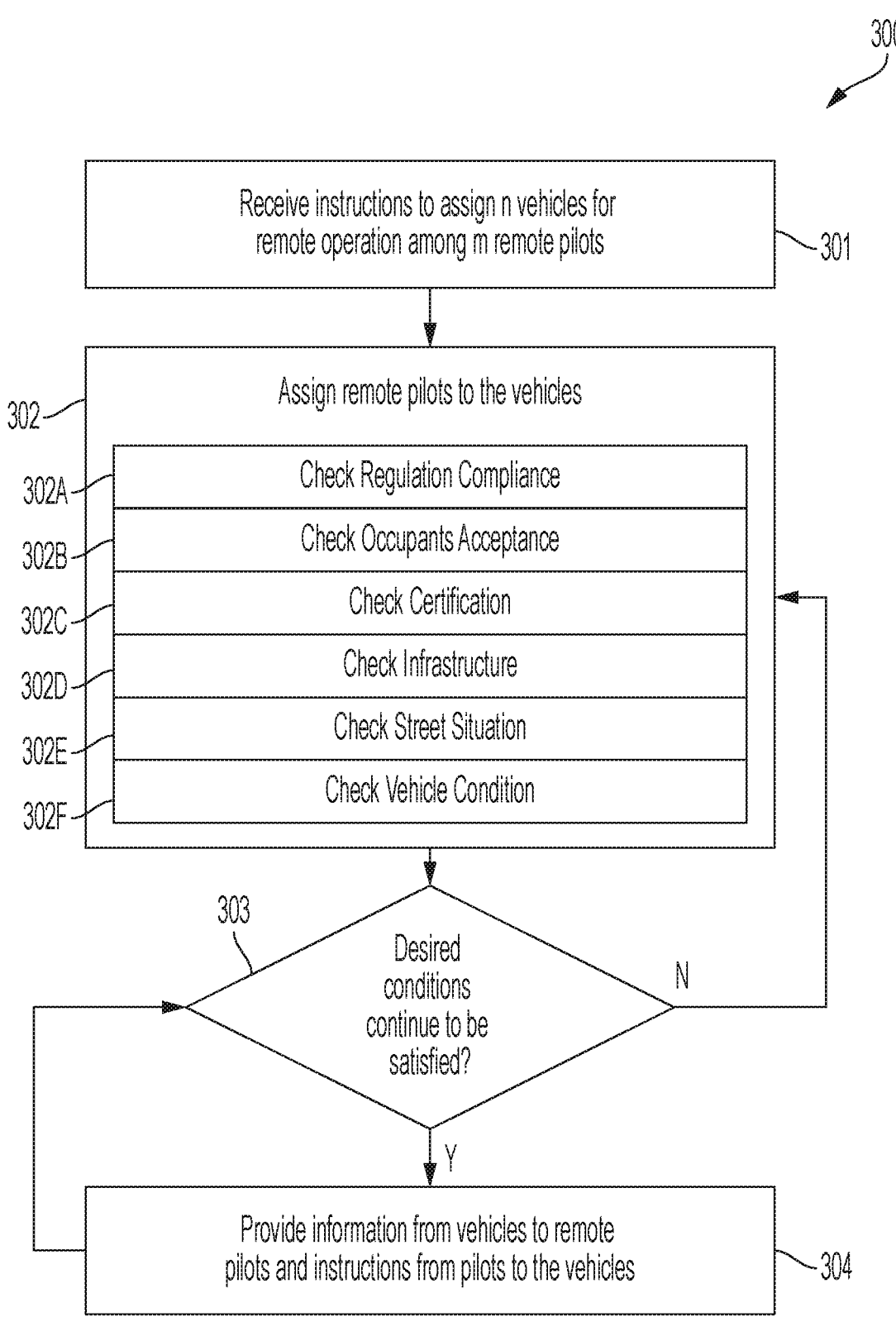
FIG. 3 depicts a flowchart of a method for monitoring and controlling multiple vehicles simultaneously by pilots according to one or more embodiments of the present invention.

FIG. 3 depicts a flowchart of a method for monitoring and controlling multiple vehicles simultaneously by pilots according to one or more embodiments of the present invention. embodiments of the present invention facilitate a first pilot 110 to control one or more vehicles 101 with other pilots 110 or autonomous Artificial Intelligence (AI)-based system (e.g., from by the controller 106). In some embodiments the first pilot 110 can control the set of vehicles 101 assigned to the first pilot 110 with assistance from the AI-based system or one or more second pilot(s) 110.

In the method 300, at block 301, the server 120 receives an instruction to assign n vehicles 101 to be remotely operated by m pilots 110 using respective remote client devices 112. Here, m and n can be different integers. In the cases where n=m, or n<m, each of the n vehicles 101 can be assigned a respective pilot 110. Technical solutions described herein address the case where n>m. Technical solutions described herein also address the technical challenges in the cases where n≤m, where an assigned pilot 110 is to be replaced, as is described herein.

In the method 300, at block 302, a first set of pilots 110 is assigned to operate the set of m vehicles 101. The assignment may be performed using predetermined criteria using a ML algorithm, such as a multi-view, multi-objective optimization.

The selection and assignment of the set of pilots 110 is based on a determination of how many vehicles each particular pilot 110 can drive at the same time safely and with optimal speed, which, in turn, is determined based on various objective functions. The objective functions can include at least compliance, occupants' acceptance, operator certification, infrastructure availability, and vehicle state. In some embodiments of the present invention, only some of the above objective criteria may be used for the selection; and in other embodiments of the present invention, additional criteria may be used.

In some embodiments of the present invention, a regulatory compliance of the selection and assignment ("assignment") is performed at block 302A. The assignment is compliant with all applicable regulations, such as the road traffic act, the air traffic (controller) law, and/or the maritime transport act that apply to remote controlled driving of vehicles 101. The regulations may specify if multiple vehicles may be controlled at the same time by a pilot 110. In some cases, the multiple controlling may depend on the vehicle type (e.g., car, truck, bus, construction machine, agricultural machine, UAV), vehicle weight, vehicle dimensions, engine power and transported goods (e.g., people, animals, dangerous goods), etc.

In some embodiments, assigning the pilot 110 to a vehicle 101 includes checking with one or more occupants (e.g., passengers) of the vehicle 101 if the pilot 110 is acceptable, at block 302B. For example, at least a predetermined number of occupants have to accept the pilot 110 for controlling the vehicle 101 (in which the occupants are seated). The occupants may be informed by the server 120 that the pilot 110 will be assigned multiple (n) vehicles n∈Q+ vehicles. The information may be passed on to the occupants via the occupants' respective electronic devices, such as phones. Alternatively, or in addition, the information may be relayed to the occupants through one or more interfaces in the vehicle 101, e.g., dashboard, infotainment, voice announcement, etc.

Further, in one or more embodiments of the present invention, assigning the pilot 110 to the vehicle 101 includes checking that the pilot 110 is certified to operate the vehicle 101, at 302C. If the pilot 110 is assigned more than one vehicle (e.g., n) 101, is checked to confirm that the pilot 110 is certified to operate at least n vehicles simultaneously. Further, the certification is checked to verify that the pilot 110 is certified to operate the n vehicles that may be of different categories $a_i$ to $a_m$, $1 \leq m \leq n$. Checking the certification of the pilot 110 includes verifying an entry of a database (e.g., department of motor vehicles database, employment database, etc.) that is a compilation of information associated with the pilot 110. The certification can include compliance of the pilot 110 with licensing requirements, number of training hours, number of apprentice hours, number of independent operating hours, and other driving history of the pilot 110. The certification related information may further include medical background of the pilot 110.

Further, the information-technology (IT) infrastructure available to the pilot 110 is checked at block 302D. The IT infrastructure is checked to ensure it facilitates the simultaneous operation of the n vehicles being assigned to the pilot 110. Verifying the capability of the IT infrastructure includes checking communication specifications available for communication between the pilot 110 (i.e., client device 112 associated with the pilot 110) and the server 120. The communications specifications checked can include comparing metrics, such as network bandwidth, network jitter, network latency, and/or any other metric associated with the communication network with predetermined thresholds. Further, the verifying includes checking the hardware and/or software specifications of the client device 112. For example, the speed, number of cores, amount of memory, power backup, display size, types and numbers of input controller(s), software versions, etc. can be determined and compared with predetermined thresholds. The predetermined thresholds are based on and can vary as the number of vehicles 101 assigned to the pilot 110 changes. If the predetermined thresholds are satisfied, the pilot 110 is assigned to operate the vehicle 101.

At block 302E, street condition or operating scenario associated with each of the m vehicles 101 is also checked. The street condition of a vehicle 101 can depend on external factors, such as weather, road condition, road design, traffic condition, terrain, speed limit, and other environmental factors.

At block 302F, a vehicle condition of the vehicle 101 is checked. The vehicle condition can include factors related to the technical design and available features of the vehicles

101. The more advanced the autonomous driving capabilities of a vehicle are, the less control or driving effort is required from the pilot 110. Thus, a pilot can monitor additional vehicles and the volume of prospective pilots increases. Further, due to the increasing synergy between the pilot 110 and autonomous features of the vehicle 101, the overall service quality can be improved.

Figure 4:
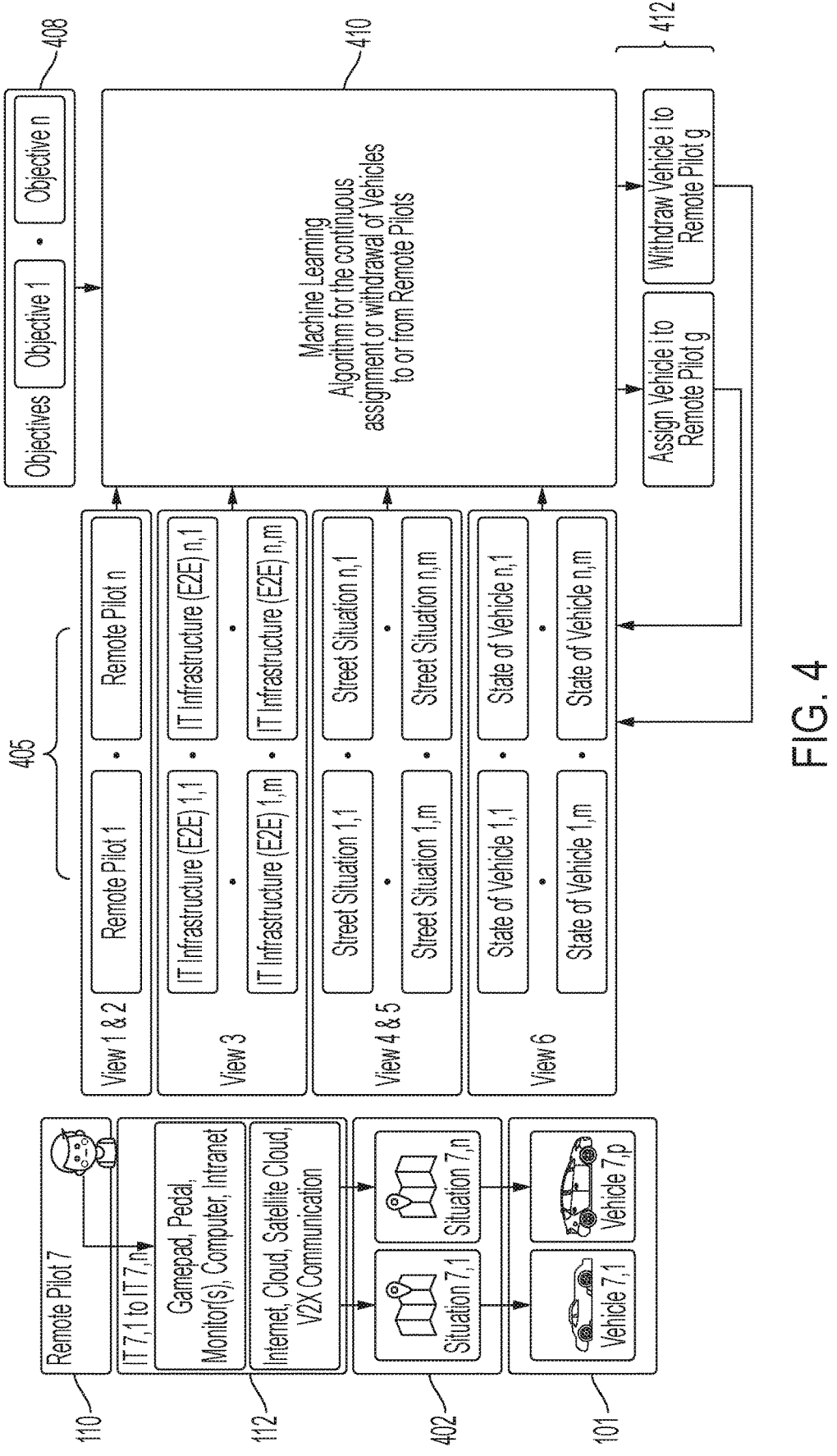
FIG. 4 depicts an operational flow diagram of using a multi-view, multi-objective optimization for assigning pilots to vehicles in a particular example scenario according to one or more embodiments of the present invention.

FIG. 4 depicts an operational flow diagram of using a multi-view, multi-objective optimization for assigning pilots to vehicles in a particular example scenario according to one or more embodiments of the present invention. From the n pilots 110, a first set of pilots 110 is selected to operate the m vehicles 101. The first set of pilots 110 can be the complete set of n pilots 110, a single pilot 110, or a subset of the pilots 110.

In the example scenario, a pilot #7 is used as an example pilot 110. The pilot #7 is shown to have a client device 112 with certain infrastructure. Further environmental conditions 402 of the vehicles 101 are also captured for the selection of the pilots 110. In the depicted scenario the pilot #7 is assigned p vehicles 101.

In one or more embodiments of the present invention, the server 120 uses a multi-view, multi-objective algorithm 410 to determine the selection and assignment of the pilots 110 and the vehicles 101. The multi-view, multi-objective algorithm 410 can be a ML algorithm. The multi-view, multi-objective algorithm 410 receives as inputs several "views" 405 and several "objectives" 408.

A "view" 405 is a representation of data associated with the pilots 110 and/or the vehicles 101. For example, each of the separate data that is captured, such as about the compliance, the certification, the infrastructure, the street situation, the vehicle state, etc. represents a distinct view 405 of the factors to be analyzed. Each of these views 405 can be analyzed in isolation or in combination with one or more other views 405.

Further, an "objective" 408 is a set of thresholds that are desired when matching a pilot 110 with a vehicle 101. The objectives 408 are input to the multi-view, multi-objective algorithm 410, for example, as rules or policies that the server 120 is to apply when making the selection and assignments. The objectives 408 may be provided electronically, for example, as part of a file, a database, a data structure, or any other such manner. In some embodiments, one or more administrators may update the objectives 408 dynamically, for example, via a user interface. The objectives #n 408 are to be optimized and satisfied simultaneously. The variables of the objectives 408 are factors that can be grouped into related groups or views.

FIGS. 5A and 5B depict an example view of several objectives used in an example scenario according to one or more embodiments of the present invention. In the depicted example, the multiple views 405 are shown as columns of the table 502 (split into 502A, and 502B), and the multiple objectives 408 are shown as rows. For example, the objectives 408 include number of vehicles assigned to one remote driver, response time of remote driver, shortest travel time, smooth journey (e.g., avoidance of potholes), and minimizing overall operating cost. Several other objectives are possible in other embodiments, which can be used alternatively or in addition to those listed.

As can be seen from FIG. 4 and the example in FIGS. 5A and 5B, apart from the ability and qualification of the pilot 110, there are other views 405 that influence the selection and assignment. For example, in FIG. 4, View 3 includes all factors that make up the end-to-end performance of the IT infrastructure. This includes the equipment of the pilot's client device 112, the fixed network connection to the workloads in the server 120 as well as to the satellite cloud-based workloads at the edge, and from there the cellular broadband connection (e.g., 5G) to the digital communication hub (i.e., the controller 104) in the vehicle 101.

Performance includes not only factors that make statements about network service qualities or locally available computer power, but also whether the appropriate peripherals and functions are available to control multiple vehicles 101 simultaneously. For example, this includes having the appropriate input controllers, such as pedals, gamepads, joysticks, steering via eyes, gestures, or verbal commands. Two further views 405 consider factors that favor or impair the trafficability of the road due to natural environmental influences (View 4) on the one hand, and due to the actual road design (View 5) on the other hand. Additionally, view 6 considers factors related to the technical design, to the use and to the condition of the vehicles 101, such as, level of autonomy supported by the controller 104 of the vehicle 101. As noted elsewhere herein, the more the autonomy, the higher the number of vehicles 101 operated (or monitored) by the pilot 110.

The integration of these heterogeneous views 405 facilitates a more accurate and robust clustering of the factors that are to be considered when selecting and assigning pilots 110 to the vehicles 101. The multi-view, multi-objective algorithm 410 aims to find clusters that are consistent across different views 405 and satisfy the objectives 408. The multi-view, multi-objective algorithm 410 can determine and provide results based on what is the variable set of interest?; what is the objective function?; and what are the set of constraints?

The variable set of interest can be determined based on the variables being used in the objectives 408. The objective function can be determined based on the views 405, which can also be considered as dimensions, and along with other criteria such as the input values (domains). The multi-view, multi-objective algorithm 410 uses such dimensions for the selection of a suitable algorithm to determine the values that can be used as thresholds (or conditions) for selecting pilot(s) 110 for a particular vehicle(s) 101. Additionally, the multi-view, multi-objective algorithm 410 identifies the set of constraints to achieve the thresholds and thus, finds feasible solutions for the assignment of pilot(s) 110 to the vehicle(s) 101.

Embodiments of the present invention facilitate implementation of the multi-view, multi-objective algorithm 410 by using infinitesimal calculus, points within the domain space with no slope of the function are called optima, which are classified into local and global minima and maxima. The technical challenge faced by the multi-view, multi-objective algorithm 410 can be represented as a challenge with several partially conflicting objectives and a larger number of factors, where a set of sub-optimal outcomes have to be eliminated, resulting in global extrema across all objectives. Embodiments of the present invention address such technical challenge using evolutionary computation, which is a sub-field of computational intelligence, a branch of ML and AI. For example, within evolutionary computing, embodiments of the present invention encode the multi-objectives of the remote pilots 110 or controllers 112 into a plurality of chromosomal representations. From these representations, the chromosomal representation solutions are ranked. An N-point crossover and mutation on the chromosomes enable the system to anneal from local optimal solutions. This enables the system to find and search, over time, the best solution within near real time requirements. Here, "chromosomal representation" can be a vector representation that facilitates deciding (1) the priority values of objectives that determine which objective is prioritizes when resource conflicts occur, and (2) modes to be selected for activities.

Referring to FIG. 4, based on the multi-view, multi-objective algorithm 410, the server 120 can determine assignment status (412) of a vehicle-i in relation to a pilot-g. For example, the assignment status 412 can include assigning the pilot-g to operate the vehicle-i; or, withdrawing the pilot-g from operating the vehicle-i. Accordingly, the multi-view, multi-objective algorithm 410 determines the compatibility of one or more remote operating clients 112 with a set of vehicles 101 by matching attributes of the one or more remote operating clients 112 with specifications associated with the vehicles 101. The specifications are the objectives 408, which may be particular to the m vehicles 101 for which remote operating pilots are to be found.

Referring to FIG. 3, the server 120 continuously monitors one or more pilots 110 to ensure that the objectives 408 are being satisfied, at block 303. For example, the continuous monitoring can include checking the biometric data of a pilot 110 at a first remote operating client 112 assigned to control a set of vehicles 101. For example, the biometric data includes at least one from Heart Rate Variability (HRV), blood sugar level, lid movement, eye movement, and beta waves, etc. The monitoring can further include checking the other views 405 (street conditions, vehicle conditions, etc.) and comparing with the objectives 408. Based on the monitoring, the server 120 may determine that the first remote operating client 112 assigned to control the set of vehicles 101 is to be replaced. In some embodiments, the objectives 408 may be changed dynamically, which triggers the first pilot 110 becoming incompatible with the set of vehicles 101 to which he/she was assigned.

In response to such detection, the server 120 identifies, from the remote operating clients 112, a second remote operating client 112 as a replacement of the first remote operating client 112. The identifying includes determining compatibility of the second remote operating client with the plurality of vehicles by using the multi-view, multi-objective algorithm 410 as described (304). Determining the compatibility of the second remote operating client 112 with the set of vehicles 101 includes matching attributes of the second remote operating client 112 with specifications associated with the vehicles 101. The second remote operating client 112 selected in place of the first can be, in some embodiments of the present invention, multiple remote operating clients 112.

Further, control of the set of vehicles 101 is reassigned to the second remote operating client 112, which provides an operation instruction to manipulate operation of the vehicles 101. Reassigning control of the set of vehicles 101 to the second remote operating client 112 can include confirming with one or more occupants of the vehicles 101 the reassignment to the second remote operating client 112.

If it is determined that a first remote pilot 110 is able to take over control/monitoring of a first remote vehicle 101, then control commands such as change of direction, acceleration or deceleration are assigned to a first remote operating client 112 associated with the first remote pilot 110. Accordingly, the first remote operating client 112 (buttons, keys, rockers, and others) can be used to operate the remote vehicle 101 henceforth, until another change/reassignment occurs. The reassignment can be indicated by vibration, sounds, or even a visualization to the first remote pilot 110 to which the control is now transferred. The first remote pilot 110 has to acknowledge and/or prove that s/he has the assignment and control of the commands under control before the reassignment is completed. For example, the first remote pilot 110 can provide the acknowledgement by simulated braking, acceleration, or curving. The system only hands over the first remote vehicle 101 to the first remote pilot 110 when, according to the current status, no interference is expected in supervising other vehicles under the first remote pilot's 110 control. If the first remote pilot 110 is unable to provide the acknowledgement, the transfer is not completed, and the first remote vehicle 101 continues to be operated as it is presently until a replacement is identified.

Conversely, in the same scenario, if a second remote pilot is released from the responsibility of monitoring the first remote vehicle 101 (during the reassignment), the assignment of control commands to the associated buttons, keys, rockers, etc. of the second remote operating client 112 of the second remote pilot 110 is released. In this case, it is possible that the system changes the assignment of remote vehicle(s) 101 that continue to be monitored to the preferences of the second remote pilot 110 or based on experience data on the control units. Again, the system will only make an adjustment if the overall situation allows it (multi-view, multi-objective). Here, the system completes the release of control from the second remote pilot 110 only after confirming that the first remote pilot 110 has obtained control of the first remote vehicle 101. In this way, the system performs a simulation check to ensure that the newly assigned remote pilot 110 has the reassignment under control before completing transfer of the control.

Referring to the flowchart of method 300, at block 304, upon assigning one or more remote pilots 110 to operate the vehicles 101 remotely, the operation of the vehicles 101 is performed by providing information from the vehicles 101 to the respectively assigned remote pilots 110. Further, operational instructions from the remote pilots 110 are provided to the vehicles 101. The flow of such communications is through the server 120 in one or more embodiments of the present invention via the one or more telecommunication networks.

The method 300 depicts a server (120) assigning and/or reassigning one or more remote pilots 110 to one or more vehicles 101. The method 300 can be triggered by one or more remote pilots 110, who are being monitored, having to be replaced. Alternatively, or in addition, the method 300 can be triggered by one or more vehicles 101 requesting a change in the remote pilots 110. Alternatively, or in addition, the method can be triggered by one or more vehicles 101 being added to or removed from the set of remote vehicles 101 that is to be assigned remote pilot(s) 110. Other reasons may trigger the method 300 in one or more embodiments of the present invention.

Providing information from multiple vehicles 101 to one or more remote pilots 110 can be technical challenge. In some cases, viewing such multiple views simultaneously can also be a challenge to the remote pilot 110 assigned to operate and monitor multiple vehicles 101. Embodiments of the present invention address such technical challenges by creation of single pane of control for optimal transport control.

Figure 6:
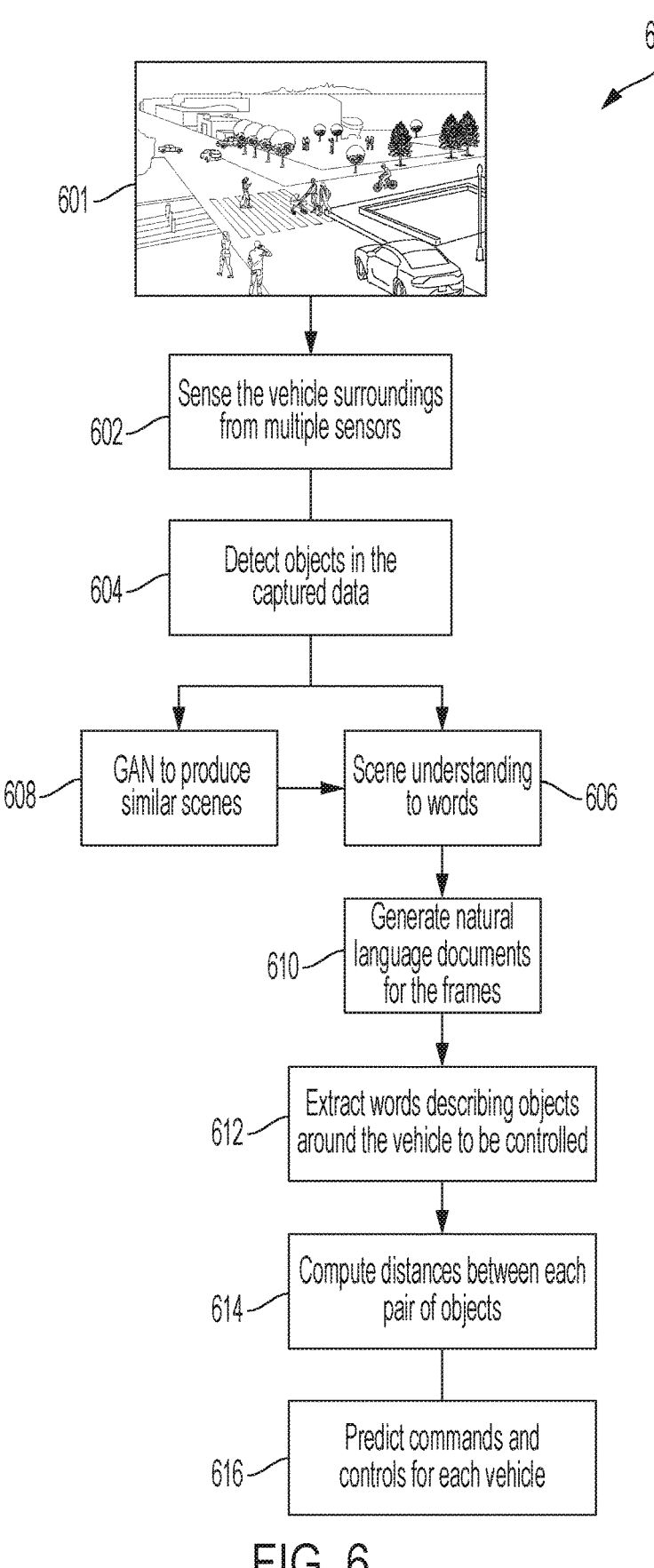
FIG. 6 depicts a flowchart of a method for creating a single pane of control for optimal transport control according to one or more embodiments of the present invention.

FIG. 6 depicts a flowchart of a method for creating a single pane of control for optimal transport control according to one or more embodiments of the present invention. The server 120 may create a single pane of control for the multiple vehicles 101 that are assigned to a particular remote pilot 110 (or a set of remote pilots 110). The single pane of control, in addition to the vehicles' 101 existing autonomy abilities, can ensure that the remote pilot 110 is alerted when a situation arises that requires increased attention. In other words, creating the single pane provides a "seeing eye" that senses potential hazards. Further, creating the single pane relieves the remote pilot 110 of information overload and allows him/her to remotely control multiple vehicles 101 safely simultaneously. In some embodiments of the invention, the creation of the single pane can be implemented at the edge or more centrally within the edge computing infrastructure.

In method 600, at block 602, the vehicle surroundings are captured using the multiple sensors (102, 106). The vehicle surroundings can be from multiple vehicles. The captured vehicle surroundings can include data streams from multiple sensors, e.g., cameras, lidars, etc. For example, the captured information can include a first data stream from a sensor 106 of a first vehicle 101, a second data stream from a sensor 106 of a second vehicle, and a third data stream from a sensor 102 that is part of the road infrastructure. The data streams can be video streams with the sensors being cameras in some examples. Alternatively, or in addition, the data streams can include volumetric streams (e.g., including point clouds), or other types of data.

At block 604, objects in the captured data are recognized and interpreted. For example, AI, ML, or other types of image processing techniques are used to detect the objects in the captured data. For example, a Convolutional Neural Network (CNN) is used to detect and recognize the objects within the captured data. Each object that is discovered is represented as a topic T, in some embodiments of the present invention. Accordingly, the video volumetric streams are converted into topics.

Further, the detected and recognized objects are processed using techniques to compute distances between natural language documents, such as computing Hierarchical Optimal Topic Transport (HOTT) distances or other such techniques to generate a sequence of frames based on the multiple data streams from the multiple sources. HOTT distances combine language information from word embeddings with corpus-specific, semantically meaningful topic distributions from Latent Dirichlet Allocation (LDA).

Further, at block 606, the interpretation of the several data streams is converted to words (i.e., text) describing the surroundings captured in the data streams. In some embodiments of the present invention, at block 608, AI model(s) are used to generate scenes similar to those captured in the data streams. For example, Generative Adversarial Network (GAN) is used to generate such artificial scenes based on the captured data streams. The artificially generated scenes are also converted to text similar to the scenes that are actually captured by the data streams.

Accordingly, the data streams (received and artificially generated), such as videos, are converted to scene understanding, i.e., understanding perceptual information depicted in the data streams and providing a textual (or machine readable) description of the perceptual information. Accordingly, a visual description of the environment is produced. For example, the visual description of a frame 601 from an example data stream can include a list of objects detected, such as baby in stroller, dog walking with man, man on cycle, two kids playing, man crossing road, etc. In some embodiments of the present invention, at block 610, a natural language document is generated for each frame from the multiple data streams. A "frame" can be a unit of information captured by the sensors (102, 106). For example, in the case of video data streams, a frame can be an image, where the video includes a sequence of such images to capture and represent motion.

For example, HOTT distances are used for comparing the natural language documents representing the frames of the captured data streams. HOTT distance between two documents indicates a similarity (or difference) between the two documents. The shorter the distance, the more similar the documents. In other embodiments other techniques are used to measure similarity between two or more natural language documents, and in turn the frames captured. HOTT distance typically compares natural language documents using optimal transport, topic modeling, and word embeddings. Once the words are extracted from a scene understanding, objects around the tele-operated vehicle 101 are extracted from the scene, at block 612. The objects "around" the tele-operated vehicle 101 can include objects that are determined to be within a predetermined distance from the vehicle 101, for example, 10 meters, 50 meters, 100 meters, etc. The distance can be measured/estimated based on the data streams, for example, using photogrammetry and image processing techniques that are known or further developed.

As noted, each object is represented as a topic T. Consider that topics identified include a set $T=\{t_1, t_2, \ldots t_{|T|}\} \subset \Delta^{|V|}$, which are distributions over words, as well as document distributions over topics. In HOTT, given an embedding of a vocabulary as $V \subset \mathbb{R}^n$, the Euclidean metric called word mover's distance (WMD) puts a geometry on the words in V. A corpus $D=\{d^1, d^2, \ldots d^{|D|}\}$ can be represented using distributions over V via a normalized bag-of-words (BOW). A BOW represents documents as vectors in $\mathbb{R}^{|V|}$, where $|V|$ is the vocabulary size; each coordinate equals the number of times a word appears.

For the corpus $D=\{d^1, d^2, \ldots d^{|D|}\}$, where $d^i$ represents an $i^{th}$ document in the corpus, the HOTT distance between documents $d^1$, $d^2$ is expressed as:

$$HOTT(d^1, d^2) = W_1\left(\sum_{k=1}^{|T|} \bar{d}_k^1 \delta_{t_k}, \sum_{k=1}^{|T|} \bar{d}_k^2 \delta_{t_k}\right),$$

Where each Dirac delta $\delta_{t_k}$ is a probability distribution supported on the corresponding topic $t_k$ and where the ground metric is WMD between topics as distributions over words. Further, $W_1$ is the 1-Wasserstein distance between two distributions. Consider two sets of points (sites), X and Y in a metric space, $X=\{x_1, \ldots, x_n\}$ and $Y=\{y_1, \ldots, y_n\}$. Let $\Delta^n \subset \mathbb{R}^{n+1}$ denote the probability simplex on n elements, and let $p \in \Delta^n$ and $q \in \Delta^m$ be distributions over X and Y. Then the 1-Wasserstein distance between p and q is:

$$W_1(p, q) = \begin{cases} \min_{\Gamma \in \mathbb{R}_+^{n \times m}} \sum_{i,j} C_{i,j}\Gamma_{i,j} \\ \text{subject to} \quad \sum_j \Gamma_{i,j} = p_i \text{ and } \sum_i \Gamma_{i,j} = q_j \end{cases},$$

Where the cost matrix C has entries $C_{i,j}=d(x_i, y_j)$, where $d(\bullet, \bullet)$ denotes the distance. The constraints allow $\Gamma$ to be interpreted as a transport plan or matching between p and q.

At block 614, HOTT distances between the pairs of frames in a sequence of frames within a data stream (e.g., video stream). The fewer changes needed from one stream to turn into another, the more likely the angles will be merged with GANs. By using the HOTT equations, the information can be used with a generative algorithm. The generative algorithm uses the output of the equations to determine how much and what type of seed to use to change the original source data streams into the target stream, which is to be displayed. The displayed stream provides a singular stream to a remote pilot 110 to control multiple vehicles 101.

At block 616, the extracted words are used to determine a potential list of commands for the vehicle 101 that is remotely controlled. In one or more embodiments of the present invention, a Feed Forward Neural Network (FFNN) is used. The FFNN is input the HOTT distances d(•, •), topic distribution before and after HOTT distances are computed, and controls (i.e., predetermined values). The output of the control based FFNN produces new controls and commands for the vehicle 101. In some embodiments of the present invention, the FFNN is specific to the vehicle 101; in other words, each tele-operated vehicle 101 has an associated FFNN, which is used to predict controls and operational instructions for that vehicle 101.

Accordingly, embodiments of the present invention facilitate generating a single display image stream based on a plurality of image streams, each image stream corresponding to a respective vehicle 101 from the multiple vehicles 101, the multiple vehicles being assigned to be controlled by one or more remote operating client 112. The vehicle receives, from the remote operating client 112, a vehicle operation instruction in response to the single display image stream being displayed by the remote operating client. The operation instruction is transmitted, to at least one vehicle 101 from the vehicles 101, to manipulate operation of the at least one vehicle 101. The operation instruction changes at least a speed and a heading of the at least one vehicle 101.

For example, the single display image stream is generated by augmenting a first image stream from the plurality of image streams with information extracted from a second image stream from the plurality of images. The information extracted from the second image stream is selected based on the information being categorized as at least one of an urgent concern, a safety concern, and a user-preference. Further, in one or more embodiments of the present invention, the single display image stream is generated by transforming the first image stream from the image streams with reference to a second image stream from the images. Here, the image streams represent the data streams that are captured by the one or more sensors (102, 106).

In the description herein, it is considered that m<<n, i.e., that there are many more vehicles 101 than remote pilots 110. Embodiments of the present invention have built in safety measures that adapt and change based on the dynamic number of remote pilots 110 and vehicles 101.

For example, consider case 1: m>=n. In this case, an equal or a greater number of remote pilots 110 are available than n vehicles 101. The assignment of remote pilots 110 to vehicles 101 is based on experience and pilot safety record vectors that are compared with a distance metric to the ideal driver experience and pilot safety record vectors based on historical vehicle record. If the vehicle 101 is new, a deep learning residual network will accept the description vector of the vehicle 101 and output an ideal driver experience and pilot safety record. An optimization algorithm assigns remote pilots 110 to the vehicles 101 where each vehicle 101 has at least one driver. If a vehicle 101 has more than 1 driver, a prioritized set of instructions is accepted based on vector similarity scores. The competition between remote pilots 110 to go up the priority board incentivizes safe driving.

Consider case 2: m<n. In this case, there are more vehicles 101 than remote pilots 110. The pilot assignment to a group of vehicles 101 is based on experience and pilot safety record vectors that are compared with a distance metric to the ideal driver experience and pilot safety record vectors based on historical vehicle record. As all remote pilots 110 are assigned to a vehicle 101, there are vehicles 101 without remote pilots 110. An agglomerative clustering algorithm creates groups of vehicles based on a multi-objective optimization criterion. Vehicles are assigned to the same group based on similar vehicle vectors and ideal driver vectors. Each group of vehicles produce a volumetric video stream that is combined within a single windowpane focused on the initial vehicle 101. Controls are sent back to the initial vehicle and converted with GANs to instructions to the other vehicles 101. Secondary window screens can focus on vehicles 101 that have an emergency or anomalous sensor reading. When this happens, the vehicle drops out of the group and waits to be assigned another remote pilot 110.

Embodiments of the present invention address several technical challenges and provide improvements and practical applications in the field of remotely operated vehicles. Embodiments of the present invention facilitate a remote pilot to control one or more vehicles simultaneously (1:n). Embodiments of the present invention facilitate several remote pilots to control one or more vehicles simultaneously (n:m). Embodiments of the present invention facilitate optimal transport to determine how much each image needs to change to be equivalent to another image. The image streams for teleoperation are changed to match a singular video such that controlling one vehicle by a remote pilot control all the remotely operated vehicles associated with the remote pilot. Further, embodiments of the present invention facilitate mapping of controls between an optimal transport scene to a raw scene.

Further, embodiments of the present invention facilitate trained machine learning system to show areas on augmented reality displays that can be identified. The system superimposes hazards or situations that are not present in reality, but to which the remote pilots have to react in time and correctly.

Further, based on biometric data (e.g., HRV, blood sugar level, lid movement, eye movement, beta waves), and the quality of the response (correctness and the reaction speed), the remote pilot can be replaced/maintained/relieved on an assignment. Alternatively, or in addition, another remote pilot/supervisor is added to assist him/her.

Embodiments of the present invention facilitate continuously determining an optimal number of remote pilots per vehicle or, conversely, the optimal number of vehicles per remote pilot using a multi-view clustering multi-objective approach.

Embodiments of the present invention facilitate converting computer vision stream of data into actionable commands for vehicles by converting video streams to scene understanding to words. Then words to distance matrix and commands for vehicle's understanding of the situation to commands. Scene understanding to Words, words to distance matrix using distance metrics, such as HOTT is used as one of the multi objective optimization in some embodiments of the present invention.

Further, embodiments of the present invention facilitate checking the compatibility of different multi views of drivers and multi objective optimization on capability of drivers with scene understanding by cameras in the vehicles.

According to one or more embodiments of the present invention, a computer-implemented method for orchestrating operation of multiple vehicles includes generating a single display image stream based on multiple image streams, each image stream corresponding to a respective vehicle from the multiple vehicles. The multiple vehicles are assigned to be controlled by a remote operating client. The method further includes receiving, from the remote operating client, a vehicle operation instruction in response to the single display image stream being displayed by the remote operating client. The method further includes transmitting, to at least one vehicle from the multiple vehicles, the operation instruction to manipulate operation of the at least one vehicle.

In one or more embodiments of the present invention, the operation instruction changes at least a speed and a heading of the at least one vehicle.

In one or more embodiments of the present invention, the generating the single display image stream further includes augmenting a first image stream from the image streams with information extracted from a second image stream from the images.

In one or more embodiments of the present invention, the information extracted from the second image stream is selected based on the information being categorized as at least one of an urgent concern, a safety concern, and a user-preference.

In one or more embodiments of the present invention, generating the single display image stream further includes transforming a first image stream from the image streams with reference to a second image stream from the images.

In one or more embodiments of the present invention, the remote operating client includes remote operating clients.

In one or more embodiments of the present invention, the image streams include a first image stream captured by an image capturing device mounted on a first vehicle from the vehicles.

In one or more embodiments of the present invention, the image streams includes a second image stream captured by an image capturing device stationed along a route of the first vehicle.

In one or more embodiments of the present invention, the vehicles are assigned to the remote operating client based on a matching matrix.

In one or more embodiments of the present invention, the method further includes generating an alert for the remote operating client to provide the operation instruction in response to detecting a potential hazard in the single display image stream using computer vision.

According to one or more embodiments of the present invention, a computer-implemented method for orchestrating operation of multiple vehicles includes detecting, based on a monitoring of a first remote operating client assigned to control the multiple vehicles, that the first remote operating client is to be replaced. Further, the method includes identifying, from multiple remote operating clients, a second remote operating client as a replacement of the first operating client, the identifying includes determining compatibility of the second remote operating client with the multiple vehicles. Further, the method includes reassigning control of the multiple vehicles to the second remote operating client, which provides an operation instruction to manipulate operation of the multiple vehicles.

In one or more embodiments of the present invention, the operation instruction changes at least a speed and a heading of the at least one vehicle.

In one or more embodiments of the present invention, the monitoring of the first remote operating client includes checking biometric data of a pilot at the first remote operating client.

In one or more embodiments of the present invention, the biometric data includes at least one from a group including Heart Rate Variability (HRV), blood sugar level, lid movement, eye movement, and beta waves.

In one or more embodiments of the present invention, determining compatibility of the second remote operating client with the multiple vehicles includes matching one or more attributes of the second remote operating client with one or more specifications associated with the multiple vehicles.

In one or more embodiments of the present invention, the one or more specifications associated with the multiple vehicles includes at least one from a group including infrastructure at the second remote operating client and certification of a pilot of the second remote operating client.

In one or more embodiments of the present invention, the first remote operating client is determined to be replaced based on an operating scenario of at least one of the multiple vehicles being incompatible with the first remote operating client.

In one or more embodiments of the present invention, the operating scenario of the at least one of the multiple vehicles includes a traffic condition, a weather, a terrain, a speed limit, and a road condition.

In one or more embodiments of the present invention, the second remote operating client includes multiple remote operating clients.

In one or more embodiments of the present invention, the reassigning control of the multiple vehicles to the second remote operating client includes confirming with one or more occupants of the multiple vehicles the reassignment to the second remote operating client.

Various aspects of the present disclosure are described by narrative text, flowcharts, block diagrams of computer systems, and/or block diagrams of the machine logic included in computer program product (CPP) embodiments. With respect to any flowcharts, depending upon the technology involved, the operations can be performed in a different order than what is shown in a given flowchart. For example, again, depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one or more storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer-readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer-readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation, or garbage collection, but this does not render the storage device as transitory because the data is not transitory while it is stored.

Figure 7:
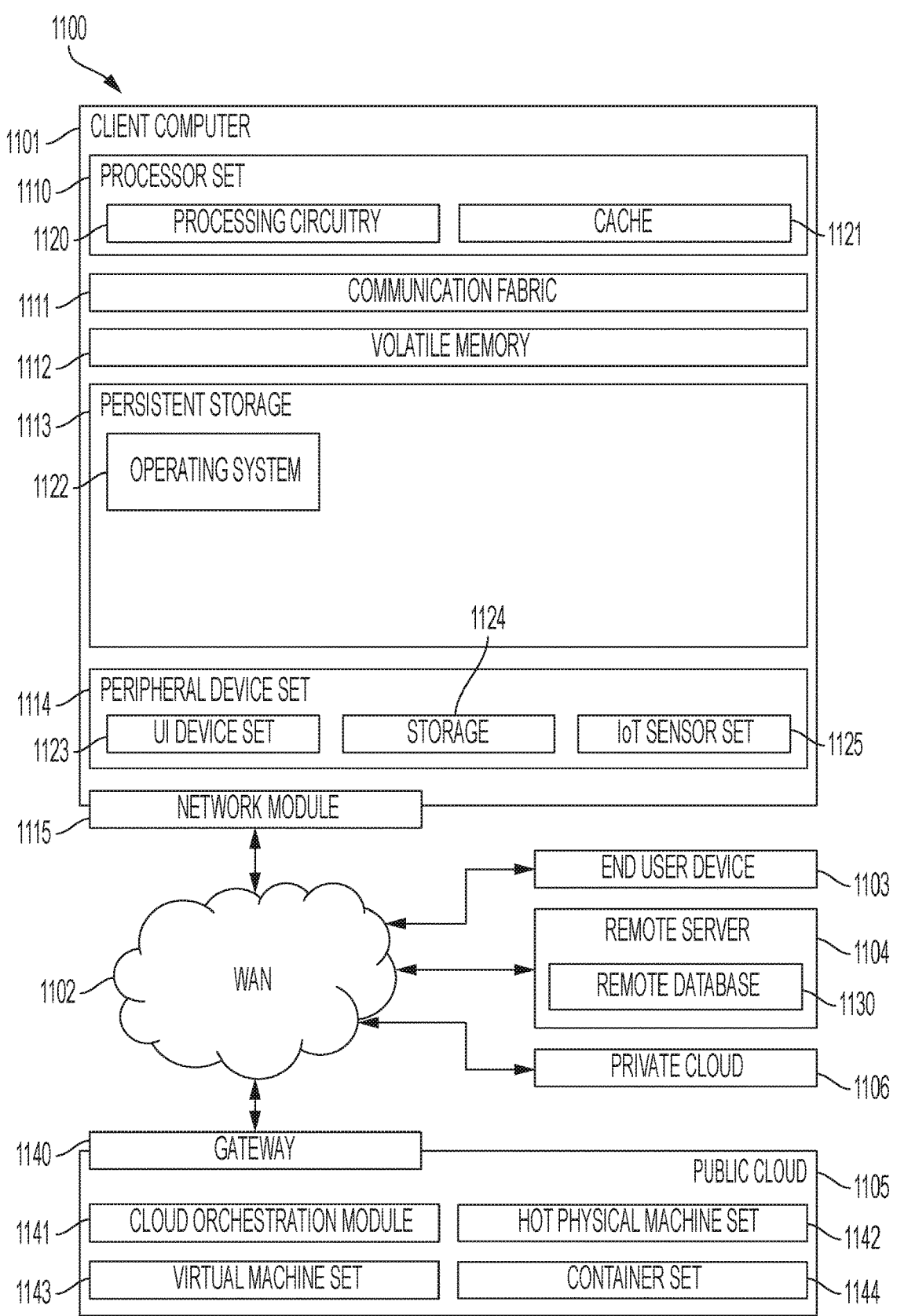
FIG. 7 depicts a computing environment in accordance with one or more embodiments of the present invention.

FIG. 7 depicts a computing environment in accordance with one or more embodiments of the present invention. Computing environment 1100 contains an example of an environment for the execution of at least some of the computer code involved in performing the inventive methods, such as assigning one or more remote pilots to a set of remotely controlled vehicles, detecting that a remote pilot needs to be replaced, generating a single data stream using data streams from several sources, etc., computing environment 1100 includes, for example, computer 1101, wide area network (WAN) 1102, end user device (EUD) 1103, remote server 1104, public cloud 1105, and private cloud 1106. In this embodiment, computer 1101 includes processor set 1110 (including processing circuitry 1120 and cache 1121), communication fabric 1111, volatile memory 1112, persistent storage 1113 (including operating system 1122, as identified above), peripheral device set 1114 (including user interface (UI), device set 1123, storage 1124, and Internet of Things (IoT) sensor set 1125), and network module 1115. Remote server 1104 includes remote database 1130. Public cloud 1105 includes gateway 1140, cloud orchestration module 1141, host physical machine set 1142, virtual machine set 1143, and container set 1144.

COMPUTER 1101 may take the form of a desktop computer, laptop computer, tablet computer, smart phone, smartwatch or other wearable computer, mainframe computer, quantum computer or any other form of computer or mobile device now known or to be developed in the future that is capable of running a program, accessing a network, or querying a database, such as remote database 1130. As is well understood in the art of computer technology, and depending upon the technology, performance of a computer-implemented method may be distributed among multiple computers and/or between multiple locations. On the other hand, in this presentation of computing environment 1100, detailed discussion is focused on a single computer, specifically computer 1101, to keep the presentation as simple as possible. Computer 1101 may be located in a cloud, even though it is not shown in a cloud. On the other hand, computer 1101 is not required to be in a cloud except to any extent as may be affirmatively indicated.

PROCESSOR SET 1110 includes one, or more, computer processors of any type now known or to be developed in the future. Processing circuitry 1120 may be distributed over multiple packages, for example, multiple, coordinated integrated circuit chips. Processing circuitry 1120 may implement multiple processor threads and/or multiple processor cores. Cache 1121 is memory that is located in the processor chip package(s) and is typically used for data or code that should be available for rapid access by the threads or cores running on processor set 1110. Cache memories are typically organized into multiple levels depending upon relative proximity to the processing circuitry. Alternatively, some, or all, of the cache for the processor set may be located "off chip." In some computing environments, processor set 1110 may be designed for working with qubits and performing quantum computing.

Computer readable program instructions are typically loaded onto computer 1101 to cause a series of operational steps to be performed by processor set 1110 of computer 1101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 1121 and the other storage media discussed below. The program instructions, and associated data, are accessed by processor set 1110 to control and direct performance of the inventive methods. In computing environment 1100, at least some of the instructions for performing the inventive methods may be stored in block 800 in persistent storage 1113.

COMMUNICATION FABRIC 1111 is the signal conduction paths that allow the various components of computer 1101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 1112 is any type of volatile memory now known or to be developed in the future. Examples include dynamic type random access memory (RAM) or static type RAM. Typically, the volatile memory is characterized by random access, but this is not required unless affirmatively indicated. In computer 1101, the volatile memory 1112 is located in a single package and is internal to computer 1101, but, alternatively or additionally, the volatile memory may be distributed over multiple packages and/or located externally with respect to computer 1101.

PERSISTENT STORAGE 1113 is any form of non-volatile storage for computers that is now known or to be developed in the future. The non-volatility of this storage means that the stored data is maintained regardless of whether power is being supplied to computer 1101 and/or directly to persistent storage 1113. Persistent storage 1113 may be a read only memory (ROM), but typically at least a portion of the persistent storage allows writing of data, deletion of data and re-writing of data. Some familiar forms of persistent storage include magnetic disks and solid state storage devices. Operating system 1122 may take several forms, such as various known proprietary operating systems or open source Portable Operating System Interface type operating systems that employ a kernel. The code included in block 800 typically includes at least some of the computer code involved in performing the inventive methods.

PERIPHERAL DEVICE SET 1114 includes the set of peripheral devices of computer 1101. Data communication connections between the peripheral devices and the other components of computer 1101 may be implemented in various ways, such as Bluetooth connections, Near-Field Communication (NFC) connections, connections made by cables (such as universal serial bus (USB) type cables), insertion type connections (for example, secure digital (SD) card), connections made though local area communication networks and even connections made through wide area networks such as the internet. In various embodiments, UI device set 1123 may include components such as a display screen, speaker, microphone, wearable devices (such as goggles and smart watches), keyboard, mouse, printer, touchpad, game controllers, and haptic devices. Storage 1124 is external storage, such as an external hard drive, or insertable storage, such as an SD card. Storage 1124 may be persistent and/or volatile. In some embodiments, storage 1124 may take the form of a quantum computing storage device for storing data in the form of qubits. In embodiments where computer 1101 is required to have a large amount of storage (for example, where computer 1101 locally stores and manages a large database) then this storage may be provided by peripheral storage devices designed for storing very large amounts of data, such as a storage area network (SAN) that is shared by multiple, geographically distributed computers. IoT sensor set 1125 is made up of sensors that can be used in Internet of Things applications. For example, one sensor may be a thermometer and another sensor may be a motion detector.

NETWORK MODULE 1115 is the collection of computer software, hardware, and firmware that allows computer 1101 to communicate with other computers through WAN 1102. Network module 1115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 1115 are performed on the same physical hardware device. In other embodiments (for example, embodiments that utilize software-defined networking (SDN)), the control functions and the forwarding functions of network module 1115 are performed on physically separate devices, such that the control functions manage several different network hardware devices. Computer readable program instructions for performing the inventive methods can typically be downloaded to computer 1101 from an external computer or external storage device through a network adapter card or network interface included in network module 1115.

WAN 1102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 1103 is any computer system that is used and controlled by an end user (for example, a customer of an enterprise that operates computer 1101), and may take any of the forms discussed above in connection with computer 1101. EUD 1103 typically receives helpful and useful data from the operations of computer 1101. For example, in a hypothetical case where computer 1101 is designed to provide a recommendation to an end user, this recommendation would typically be communicated from network module 1115 of computer 1101 through WAN 1102 to EUD 1103. In this way, EUD 1103 can display, or otherwise present, the recommendation to an end user. In some embodiments, EUD 1103 may be a client device, such as thin client, heavy client, mainframe computer, desktop computer and so on.

REMOTE SERVER 1104 is any computer system that serves at least some data and/or functionality to computer 1101. Remote server 1104 may be controlled and used by the same entity that operates computer 1101. Remote server 1104 represents the machine(s) that collect and store helpful and useful data for use by other computers, such as computer

1101. For example, in a hypothetical case where computer 1101 is designed and programmed to provide a recommendation based on historical data, then this historical data may be provided to computer 1101 from remote database 1130 of remote server 1104.

PUBLIC CLOUD 1105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 1105 is performed by the computer hardware and/or software of cloud orchestration module 1141. The computing resources provided by public cloud 1105 are typically implemented by virtual computing environments that run on various computers making up the computers of host physical machine set 1142, which is the universe of physical computers in and/or available to public cloud 1105. The virtual computing environments (VCEs) typically take the form of virtual machines from virtual machine set 1143 and/or containers from container set 1144. It is understood that these VCEs may be stored as images and may be transferred among and between the various physical machine hosts, either as images or after instantiation of the VCE. Cloud orchestration module 1141 manages the transfer and storage of images, deploys new instantiations of VCEs and manages active instantiations of VCE deployments. Gateway 1140 is the collection of computer software, hardware, and firmware that allows public cloud 1105 to communicate through WAN 1102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 1106 is similar to public cloud 1105, except that the computing resources are only available for use by a single enterprise. While private cloud 1106 is depicted as being in communication with WAN 1102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 1105 and private cloud 1106 are both part of a larger hybrid cloud.

The present invention can be a system, a method, and/or a computer program product at any possible technical detail level of integration. The computer program product can include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer-readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer-readable program instructions by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer-readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions can also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for orchestrating operation of a plurality of vehicles, the computer-implemented method comprising:

detecting, based on a monitoring of a first remote operating client assigned to control the plurality of vehicles, that the first remote operating client is to be replaced, wherein the monitoring comprises checking biometric data of a pilot at the first remote operating client and determining a state of the pilot;

identifying, from a plurality of remote operating clients, a second remote operating client as a replacement of the first remote operating client, the identifying comprising determining compatibility of the second remote operating client with the plurality of vehicles, wherein determining compatibility of the second remote operating client with the plurality of vehicles comprises matching one or more attributes of the second remote operating client with one or more specifications associated with the plurality of vehicles; and reassigning control of the plurality of vehicles to the second remote operating client, which provides an operation instruction to manipulate operation of the plurality of vehicles, wherein reassigning control comprises completing the reassigning control based on confirming that the second remote operating client has obtained control of at least one vehicle of the plurality of vehicles, wherein the confirming comprises receiving, from the second remote operating client, at least one of simulated braking, simulated acceleration, and simulated curving.

2. The computer-implemented method of claim 1, wherein the operation instruction changes at least a speed and a heading of at least one of the plurality of vehicles.

3. The computer-implemented method of claim 1, wherein the monitoring comprises checking biometric data of a pilot at the first remote operating client; and wherein determining the state of the pilot comprises determining that the state comprises at least one from a predetermined list comprising awake, tired, sleepy, and needs-rest.

4. The computer-implemented method of claim 3, wherein the biometric data comprises at least one from a group comprising Heart Rate Variability (HRV), blood sugar level, lid movement, eye movement, and beta waves.

5. The computer-implemented method of claim 1, wherein the one or more specifications associated with the plurality of vehicles comprises at least one from a group comprising infrastructure at the second remote operating client and certification of a pilot of the second remote operating client.

6. The computer-implemented method of claim 5, wherein the infrastructure at the second remote operating client has a verifying capability that includes checking communication specifications; and wherein the communication specifications comprise a network bandwidth, a network jitter, and a network latency.

7. The computer-implemented method of claim 1, wherein the first remote operating client is determined to be replaced based on an operating scenario of at least one of the plurality of vehicles being incompatible with the first remote operating client.

8. The computer-implemented method of claim 7, wherein the operating scenario of the at least one of the plurality of vehicles comprises a traffic condition, a weather condition, a terrain condition, a speed limit, and a road condition.

9. The computer-implemented method of claim 1, wherein the second remote operating client comprises a plurality of remote operating clients.

10. The computer-implemented method of claim 1, wherein the reassigning control of the plurality of vehicles to the second remote operating client comprises confirming with one or more occupants of the plurality of vehicles the reassignment to the second remote operating client.

11. A system comprising:

a computer server configured to orchestrate remote operation of a plurality of vehicles by performing a computer-implemented method that comprises:

detecting, based on a monitoring of a first remote operating client assigned to control the plurality of vehicles, that the first remote operating client is to be replaced, wherein the monitoring comprises checking biometric data of a pilot at the first remote operating client and determining a state of the pilot;

identifying, from a plurality of remote operating clients, a second remote operating client as a replacement of the first remote operating client, the identifying comprising determining compatibility of the second remote operating client with the plurality of vehicles, wherein determining compatibility of the second remote operating client with the plurality of vehicles comprises matching one or more attributes of the second remote operating client with one or more specifications associated with the plurality of vehicles; and reassigning control of the plurality of vehicles to the second remote operating client, which provides an operation instruction to manipulate operation of the plurality of vehicles, wherein reassigning control comprises completing the reassigning control based on confirming that the second remote operating client has obtained control of at least one vehicle of the plurality of vehicles, wherein the confirming comprises receiving, from the second remote operating client, at least one of simulated braking, simulated acceleration, and simulated curving.

12. The system of claim 11, wherein the biometric data comprises at least one from a group comprising Heart Rate Variability (HRV), blood sugar level, lid movement, eye movement, and beta waves.

13. The system of claim 11, wherein the one or more specifications associated with the plurality of vehicles comprises at least one from a group comprising infrastructure at the second remote operating client and certification of a pilot of the second remote operating client.

14. The system of claim 11, wherein the first remote operating client is determined to be replaced based on an operating scenario of at least one of the plurality of vehicles being incompatible with the first remote operating client, wherein the operating scenario of the at least one of the plurality of vehicles comprises a traffic condition, a weather condition, a terrain condition, a speed limit, and a road condition.

15. The system of claim 11, wherein the second remote operating client comprises a plurality of remote operating clients.

16. A computer program product comprising a memory device with computer-executable instructions therein, the computer-executable instructions when executed by a processing unit perform a method to orchestrate remote operation of a plurality of vehicles, the method comprising:

detecting, based on a monitoring of a first remote operating client assigned to control the plurality of vehicles, that the first remote operating client is to be replaced, wherein the monitoring comprises checking biometric data of a pilot at the first remote operating client and determining a state of the pilot;

identifying, from a plurality of remote operating clients, a second remote operating client as a replacement of the first remote operating client, the identifying comprising determining compatibility of the second remote operating client with the plurality of vehicles, wherein determining compatibility of the second remote operating client with the plurality of vehicles comprises matching one or more attributes of the second remote operating client with one or more specifications associated with the plurality of vehicles; and reassigning control of the plurality of vehicles to the second remote operating client, which provides an operation instruction to manipulate operation of the plurality of vehicles, wherein reassigning control comprises completing the reassigning control based on confirming that the second remote operating client has obtained control of at least one vehicle of the plurality of vehicles, wherein the confirming comprises receiving, from the second remote operating client, at least one of simulated braking, simulated acceleration, and simulated curving.

17. The computer program product of claim 16, wherein the biometric data comprises at least one from a group comprising Heart Rate Variability (HRV), blood sugar level, lid movement, eye movement, and beta waves.

18. The computer program product of claim 16, wherein the one or more specifications associated with the plurality of vehicles comprises at least one from a group comprising infrastructure at the second remote operating client and certification of a pilot of the second remote operating client.

19. The computer program product of claim 16, wherein the first remote operating client is determined to be replaced based on an operating scenario of at least one of the plurality of vehicles being incompatible with the first remote operating client, wherein the operating scenario of the at least one of the plurality of vehicles comprises a traffic condition, a weather condition, a terrain condition, a speed limit, and a road condition.

20. The computer program product of claim 16, wherein the second remote operating client comprises a plurality of remote operating clients.

\* \* \* \* \*